United States Patent [19]

Meyers et al.

[11] Patent Number: 5,286,250
[45] Date of Patent: Feb. 15, 1994

[54] KNEE JOINT HINGE FOR BRACE

[76] Inventors: Andrew H. Meyers, 31 The Birches, Roslyn Estates, N.Y. 11576; Roland J. Christensen, 192 E. 100 N, Fayette, Utah 84630

[21] Appl. No.: 890,800

[22] Filed: Jun. 1, 1992

[51] Int. Cl.$^5$ .............................................. A61F 5/00
[52] U.S. Cl. ...................................... 602/16; 602/26
[58] Field of Search ........................ 602/5, 16, 23, 26

[56] References Cited

U.S. PATENT DOCUMENTS

| | | | |
|---|---|---|---|
| 3,779,654 | 12/1973 | Horne | 602/16 X |
| 3,902,482 | 9/1975 | Taylor | 602/16 |
| 4,463,751 | 8/1984 | Bledsoe | 602/16 |
| 4,655,201 | 4/1987 | Pirmantgen | 602/16 |
| 4,723,539 | 2/1988 | Townsend . | |
| 4,773,404 | 9/1988 | Townsend . | |
| 4,802,466 | 2/1989 | Meyers et al. . | |
| 4,890,607 | 1/1990 | Townsend . | |
| 5,009,223 | 4/1991 | DeFonce | 602/16 |
| 5,107,824 | 4/1992 | Rogers et al. | 602/26 X |

OTHER PUBLICATIONS

"External Knee Joint Design Based on Normal Motion", the *Journal of Rehabilitation Research and Development*, vol. 22, No. 1, 1985, BPR 10-41 pp. 9-22, by P. S. Walker, Ph.D.; H. Kurosawa, M.D.; J. S. Rovick, M.A.; R. A. Zimmerman, B.S.

*Primary Examiner*—Richard J. Apley
*Assistant Examiner*—Linda C. M. Dvorak
*Attorney, Agent, or Firm*—Foley & Lardner

[57] ABSTRACT

A hinge having first and second plates each having a plurality of cam slots therein and being connected to upper and lower portions of a brace. The hinge also includes cam pin followers which are connected to the first and second plates and the lower portion of the brace such that they cooperate with the cam slots allowing the lower portion of the brace to rotate through a predetermined angular range relative to the upper portion of the brace with a constantly changing axis of rotation.

19 Claims, 4 Drawing Sheets

KNEE JOINT HINGE FOR BRACE

BACKGROUND OF THE INVENTION

1. Field of the Invention

The present invention relates to orthopedic devices for the stabilization and control of a human knee joint which has been injured. More particularly, the invention relates to a hinge for a knee brace which will permit the user a relatively high degree of freedom in the use of the bones while, at the same time, permitting control of the knee joint so as to optimize healing and stability.

2. Description of the Related Art

Devices for adding support and strength to the knee joint, such as that disclosed in U.S. Pat. No. 4,802,466, which is hereby incorporated by reference, have been known for decades and have taken many different forms. While substantially all of these devices have been purported to have mechanical joints designed to produce a smooth articulation of the mechanical joint that is matched to the behavior of the natural human knee joint, very few have, in fact, done so since most known devices have apparently taken for granted that the relative movement of the femur and tibia is a rotation about a single center of rotation, typically in the center of the knee. However, studies have shown that a single pivot movement does not emulate the relative movement of the femur and tibia, and that to do so a mechanical joint must produce a rearward movement of the tibia relative to the femur throughout the full flexion range of the tibia, or for whatever angle may be traversed as limited by the injury or natural limitations of the knee brace wearer.

Attempts have been made in prior art devices to more closely mimic the natural movement of the human knee joint such as the devices disclosed in U.S. Pat. Ser. Nos. 4,723,539, 4,773,404 and 4,890,607. In each of these patents, a multiaxis controlled motion knee orthosis is disclosed having a joint that is designed to constrain the tibia to slide rearwardly relative to the femur for a predetermined distance throughout an initial range of flexion of the knee from a straight leg position, and, beyond that initial range of flexion, to rotate relative thereto along a predetermined arcuate path irrespective of the loading applied to the joint by the leg of the wearer.

Therefore, in each of these devices, the tibia slides rearwardly such that its axis of rotation is constantly changing only for an initial portion of the full range of flexion of the knee. After this initial portion of flexion movement has been obtained, the tibia no longer slides rearwardly, and instead rotates about a single axis throughout the remaining portion of flexion movement. Accordingly, while these devices more closely operate like a natural knee joint as compared to the single center of rotation devices, they are still deficient in mimicking the natural knee joint in which the tibia continually slides rearward during the entire flexion movement producing a constantly changing axis of rotation of the tibia relative to the femur.

Moreover, the above devices fail to take into account the fact that during the full range of flexion motion, the medial side of the knee first moves anteriorly prior to moving posteriorly, while the lateral side of the knee continually moves posteriorly during the full range of flexion movement.

SUMMARY OF THE INVENTION

In view of the foregoing, it is an object of the present invention to provide a knee joint hinge for a brace which generates a motion similar to the natural motion of the human knee concerning the relative movement of the tibia with respect to the femur.

Another object of the invention is to provide a knee joint hinge for a brace which restricts any unwanted movement in the hinge so as not to impair the healing of an injured knee or to cause injury to the knee due to the unwanted movement.

Still a further object of the invention is to provide a knee joint hinge which is very strong and which is able to move smoothly such that binding is prevented.

Yet another object of the invention is to provide a knee joint hinge for a brace which compensates for the respective movements of the medial and lateral sides of the knee during flexion movement.

The above objects are met by providing a hinge for a brace which has an upper portion and a lower portion, the hinge having first and second plates, each having a plurality of cam slots and being connected to the upper and lower portions of the brace. The hinge also includes a plurality of cam pin followers each being connected to the first and second plates and to the lower portion of the brace such that the cam pin followers and the cam slots cooperate to allow the lower portion of the brace to rotate through a predetermined angular range relative to the upper portion of the brace, whereby an axis of rotation of the lower portion of the brace is constantly changing as the lower portion of the brace moves throughout the predetermined angular range. Additionally, a first cam slot of the plurality of cam slots in each of the first and second plates has a first segment which is substantially transverse relative to the longitudinal direction of the lower portion of the brace, and a second segment which is directed away from the first segment at an obtuse angle.

The above objects are also met by providing a hinge for a brace having an upper portion and a lower portion, the hinge having first and second plates each having a plurality of cam slots therein and being connected to the upper and lower portions of the brace. The hinge also includes a plurality of cam pin followers each being connected to the first and second plates and the lower portion of the brace such that the plurality of cam pin followers cooperate with the plurality of cam slots in the first and second plates which permits the lower portion of the brace to rotate through a predetermined angular range relative to the upper portion of the brace such that during an initial angle of rotation the lower portion of the brace moves posteriorly a first distance relative to the upper portion of the brace, and during a rotation of the lower portion of the brace beyond the initial angle of rotation and up to the end of the predetermined angular range, the lower portion of the brace moves posteriorly a second distance relative to the upper portion of the brace. Additionally, a first cam slot of the plurality of cam slots in each of the first and second plates has a first segment which is substantially transverse relative to the longitudinal direction of the lower portion of the brace, and a second segment which is directed away from the first segment at an obtuse angle.

BRIEF DESCRIPTION OF THE DRAWINGS

Other objects, features and advantages of the present invention will become apparent from the following detailed description and accompanying drawings wherein.

DETAILED DESCRIPTION OF THE PREFERRED EMBODIMENTS

Figure 1A:
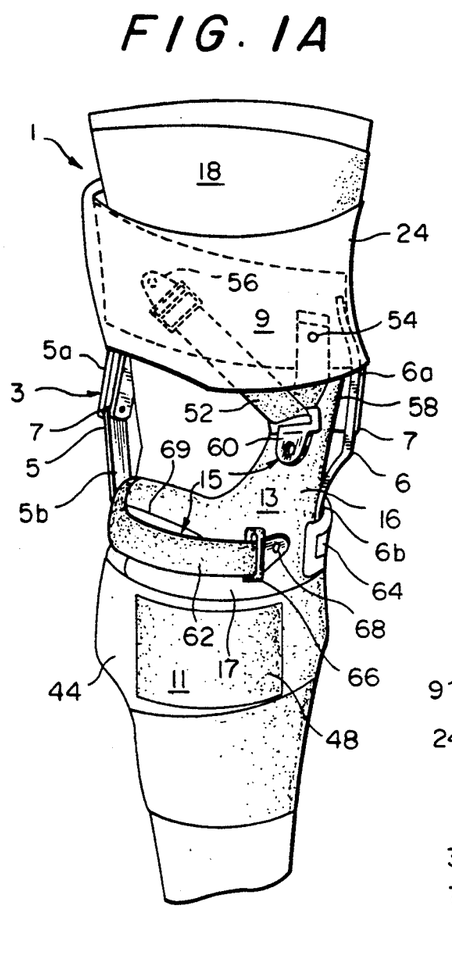
FIG. 1A is a front view of an orthotic device, showing schematically the inventive hinge, which is completely fitted onto the leg of a wearer.
Figure 2A:
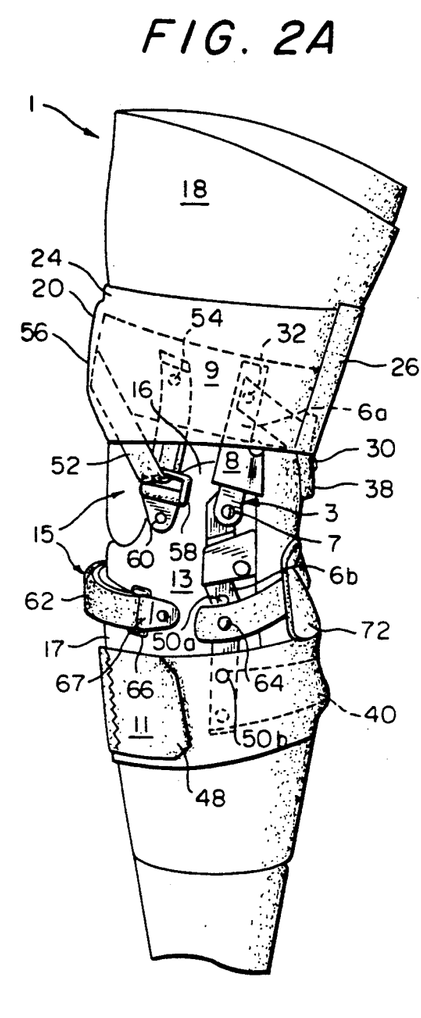
FIG. 2A is an inner side view of the orthotic device illustrated in FIG. 1A, illustrating how the condyle pad assembly covers the inner condyle region of the leg of the wearer.
Figure 2B:
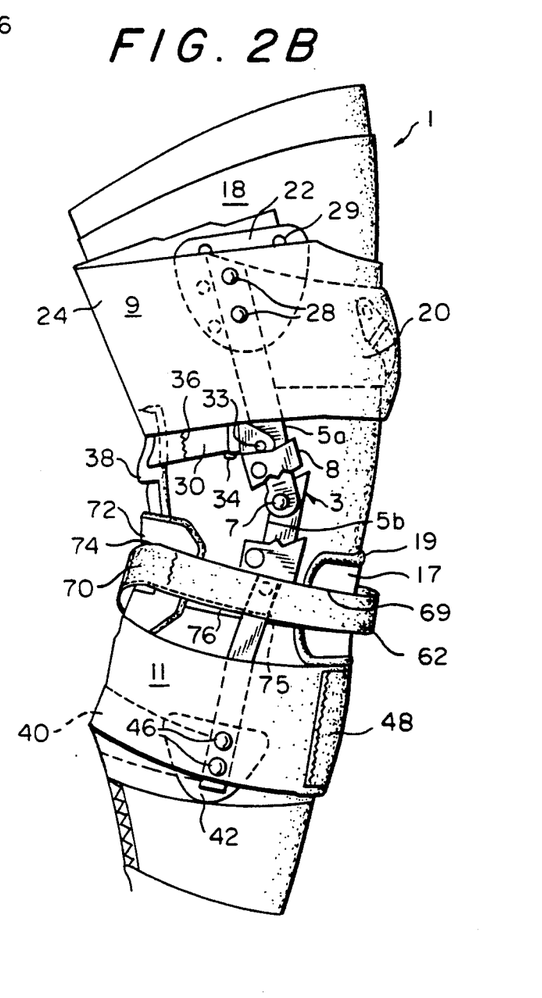
FIG. 2B is an outer side view of the orthotic device illustrated in FIG. 1A.

With reference to FIGS. 1A and 2b, a knee orthosis 1 includes a mechanical joint structure 3 formed from a pair of metallic sidebars 5, 6 that are preferably made from either stainless steel or aluminum. Alternatively, the sidebars 5, 6 can be made from a composite material such as a graphite composite. Each of the sidebars 5, 6 has an upper portion 5a, 6a and a lower portion 5b, 6b, respectively, between which hinge structure 7, shown schematically, is positioned to be alignable with the knee joint of the wearer. Each of the hinge structures 7 of the sidebars 5, 6 is preferably surrounded by a sleeve 8 formed from a resilient sheet material, such as foam neoprene. These sleeves 8 prevent the clothing of the wearer from becoming caught and bound within the moving components of the hinge structures 7 of the sidebars 5, 6.

Figure 1B:
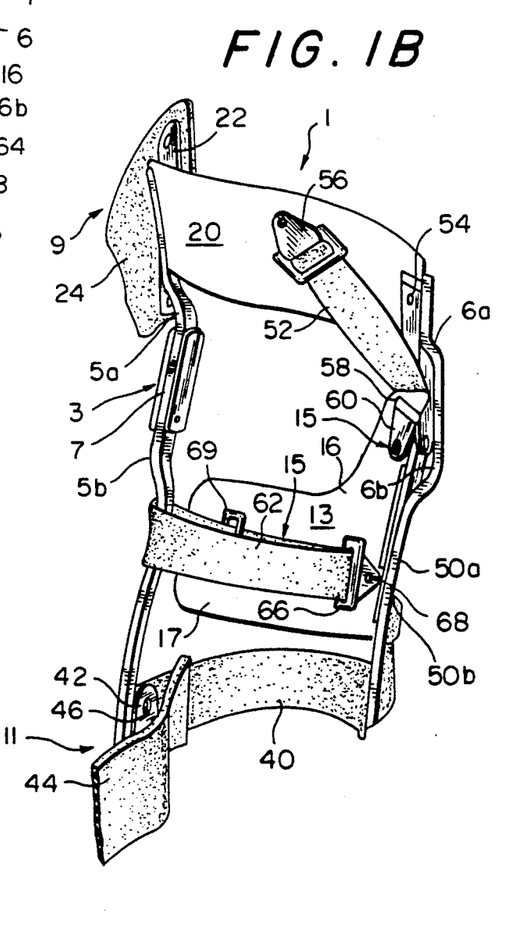
FIG. 1B is the orthotic device illustrated in FIG. 1A as it appears without the leg of a wearer and having the exterior foam neoprene straps rolled back.

With reference to FIGS. 1A and 1B, upper and lower support assemblies 9, 11 surround the lower thigh and upper calf of the wearer and support the mechanical joint structure 3 into alignment with the knee. As will be described in detail hereinafter, a condyle pad assembly 13 is disposed between the upper and lower support assemblies 9 and 11 by a mounting means indicated generally at 15. The condyle pad assembly 13 is a generally L-shaped structure having an outer surface formed from flexible but relatively stiff sheet material such as Polyethylene. At its upper end, the condyle pad assembly 13 includes a condyle supporting portion 16 which engages the inner condyle region of the leg of the wearer when the orthosis is completely installed thereon. At its lower end, the condyle pad assembly 13 includes an anterior extension 17 which engages the upper tibia of the knee joint of the wearer. The elasticity and specific V-shaped configuration of the straps forming the mounting means 15 maintain the upper end of the condyle supporting portion 16 of the assembly 13 in intimate supporting contact with the inner condylar region of the knee throughout the entire range of knee movement, while at the same time keeping the interior extension 17 engaged against the tibia of the wearer, thereby preventing tibial displacement. The simultaneous support given to both the inner condylar region and the upper tibia of the knee joint eliminates many of the most common knee instabilities associated with a structure which is minimal in size, weight and complexity. Finally, a stocking 18 slipped over the knee joint of the wearer coacts with a foam neoprene lining 19 which is adhered under the condyle pad assembly 13 in order to eliminate slippage between the pad assembly 13 and the knee joint of the wearer. Moreover, the condyle pad can be positioned such that the anterior extension 17 engages either the front portion of the lower leg or the back portion thereof.

With reference to FIGS. 1B, 2A and 2B, the upper support assembly of the orthosis 1 includes a C-shaped band 20 formed from a material that is strong yet light, such as any one of a number of commercially available graphite composites. In the preferred embodiment, the interior of this C-shaped band 20 is molded to conform to the specific contours of the upper thigh of the wearer. The C-shaped band 20 is further slightly twisted with respect to the longitudinal axis of the leg so that its outer end is higher than its inner end when the upper support assembly 9 is installed. Such shaping of the C-shaped band 20 helps to prevent it from sliding downwardly toward the knee joint of the wearer as a result of the downward and lateral forces applied to it by the V-shaped elastic strap of the mounting means 15.

As is best seen in FIG. 2B, a triangular lateral pad 22 is riveted to the inside of the outer end of the C-shaped band 20, while the upper portion 5A of the sidebar is riveted to the outside of this area of the band 20. The end of a foam neoprene mounting strap 24 is further affixed to the inside surface of the triangular lateral pad 22. As may best be seen in FIG. 2A, the outer end of this strap 24 includes a Velcro ® fastener 26 (best seen in FIG. 2A) that allows the strap 24 to be wound at least one and one-half times around the upper thigh of the wearer and then fastened upon itself. A pair of mounting rivets 28 extend through the outer end of the C-shaped band 20 to firmly sandwich the outer end of the C-shaped band 20 between the upper end of the sidebar 5a and the triangular lateral pad 22 on its inside, while other mounting rivets 29 are used to secure the fixed end of the strap 24 to the inner surface of the lateral pad 22. Other mounting rivets 29 secure the inner end of the strap 24 to the inner surface of the lateral pad 22 through a second Velcro ® fastening device (not shown). This arrangement renders the inner end of the strap 24 detachably removable from the lateral pad 22 so that it may be easily replaced upon wearing out.

The last component of the upper support assembly 9 is a posterior mounting strap 30 best seen in FIGS. 2A and 2B. The inner end of the strap 30 is anchored to the outside of the inner sidebar 6 by means of a rivet 32. The outer end of the strap 32 loops around a D-ring 34 that is connected onto the outer sidebar 5 by means of another rivet 33. Like the previously described neoprene strap 24, the posterior mounting strap 30 also includes a Velcro ® fastener 35 at its outer end. However, unlike the strap 24, the posterior mounting strap 30 is preferably formed from a relatively unresilient sheet material, such as nylon webbing. Finally, the posterior mounting strap 36 includes a pressure pad 38 for uniformly distributing the pressure that the strap 30 applies to the posterior portion of the lower thigh when the orthosis 1 is installed. In operation, both the foam neoprene strap 24 and the posterior mounting strap 30 co-act to maintain the C-shaped band 20 of the upper support assembly 9 firmly in place around the upper thigh of the wearer. By covering the various straps and buckles of the upper portion of the mounting means 15 of the condyle pad assembly 13, the foam strap 24 serves the additional function of providing a smooth exterior surface for the upper support assembly 9 that will not snag or bind on any clothing of the wearer of the orthosis 1.

As is best seen in FIGS. 1B, 2A and 2B, the lower support assembly 11 of the orthosis 1 of the invention also includes a C-shaped band 40. The outer end of the band 40 is connected to both a triangular lateral pad 42 and the lower portion 5b of the outer sidebar 5. The inner end of another foam neoprene strap 44 is connected to the inner surface of the triangular lateral pad 42 through another Velcro ® fastener (not shown). Mounting rivets 46 firmly sandwich the outer end of the C-shaped band 40 between the lower portion 5b of the sidebar 5 on its exterior and the triangular lateral pad 42 on its interior, while the inner end of the neoprene strap 44 is detachably connected to the inner surface of the triangular lateral pad 42 by means of another Velcro ® fastener (not shown). of course, the positioning of the C-shaped band 40 and the strap 44 could be reversed so that the C-shaped band is in an anterior position. Additionally, as is best seen in FIGS. 2A and 2B, the outer end of the neoprene strap 44 terminates in still another Velcro ® fastener 48 in order to render this end of the strap 44 detachably connectable to itself. Like strap 24, strap 44 is preferably capable of wrapping around the leg of the wearer as well as to provide a smooth exterior surface for the lower support assembly 11.

In an alternative embodiment, the triangular lateral pad 22 can be deleted by integrally forming the upper sidebar portions 5a, 6a with the c-shaped band 20. In this embodiment, one end of the neoprene mounting strap 24 would be affixed to the inside surface of the c-shaped band 20 by, for example, a Velcro ® fastener, while the opposite end fastens upon itself. Moreover, the posterior mounting strap 30 can alternatively be connected to the inner and outer sidebars 5, 6 by passing through a respective slot which is disposed in each upper sidebar portion 5a, 6a. The posterior mounting strap 30 would also include a Velcro ® fastener at each end such that after passing through a respective slot, the posterior mounting strap 30 can fasten to itself.

With respect to the lower support assembly 11, the c-shaped band 40 can alternatively be integrally formed with the lower sidebar portions 5b, 6b eliminating the need for the triangular lateral pad 42. In addition, instead of a neoprene strap 44, a mounting strap similar to the aforementioned posterior mounting strap 30 can be used. This mounting strap would pass through slots in the lower sidebar portions 5b, 6b and would have a Velcro ® fastener at each end such that after passing through the slots the ends can be fastened to the mounting strap.

With reference to FIGS. 1A and 1B, the purpose of the mounting means 13 is to both mount the L-shaped condyle pad assembly 13 within the knee orthosis 1, as well as to maintain this pad in intimate supporting contact with both the inner condylar region of the knee and the upper tibia of the wearer. To this end, the mounting means 13 includes a pair of rivets 50a, 50b for connecting the inner edge of the lower portion of the L-shaped condyle pad assembly 13 to the inner sidebar 6. In order to maintain the condyle supporting portion 16 of the pad 13 into supporting contact with the condylar region of the knee of the wearer, the mounting means 15 further includes a V-shaped elastic strap 52 that is connected to two points along the upper C-shaped band 20 by rivet 54 and pivoting buckle 56, respectively. The mid-portion of this V-shaped elastic strap 52 extends through the D ring 58 of a pivoting buckle 60 connected to the upper end of the pad 13. In operation, the elastic strap 52 applies an inwardly and upwardly directed force to the condyle supporting portion 16 of the pad 13 in order to maintain it firmly against the inner condylar region of the knee. The sliding engagement between the D ring 58 and the central portion of the strap 52 maintains this inwardly and upwardly directed supporting force at approximately the same angle with respect to the inner condylar region of the knee despite the pivoting motion between the strap and the pad assembly 13 caused by the flexing of the knee of the wearer. In the preferred embodiment, the elastic properties of the V-shaped strap 52 are chosen so that the magnitude (as opposed to the angle) of the inwardly and upwardly directed force applied to the condyle supporting portion 16 either stays the same or increases as the knee is bent.

Finally, with reference to FIGS. 1B, 2A and 2B, the mounting means 15 of the orthosis I also includes a strap 62 for maintaining the anterior extension of the condyle pad assembly 13 into intimate supporting engagement with the tibia of the wearer. One end of the strap 62 is anchored to the inner sidebar 6 of the orthosis 1 by means of rivet 64, while the other end of the strap 62 is threaded through the D ring 66 of a pivoting buckle 67 mounted onto the lower end of the pad assembly 13. A guide ring 69 is further provided on the lower end of the pad assembly 13 for maintaining the alignment of the strap 62. The outer end of the strap 62 includes a Velcro ® fastener 70 which allows the strap 62 to be detachably connected to either itself or another Velcro ® fastener at its posterior portion. A pressure pad 72 is included on the posterior strap 62 for the same reasons given with respect to the pressure pad 38. In order to prevent the sidebar 5 from moving with respect to the strap 62, a lateral support strap 74 (shown in FIG. 2B) is connected to the sidebar 5 by a rivet 75. This relatively short strap 74 is sandwiched between the overlapping portions of the strap 62, and includes a Velcro ® fastener 76 on both of its sides to allow it to securely fasten itself between the overlapping portions of strap 62.

In operation, the combination of the V-shaped elastic strap 52 and the strap 62 of the mounting means 15 dynamically cause the condyle supporting portion 16 and the anterior extension 17 of the L-shaped condyle pad assembly 13 to come into intimate supporting contact against the inner condylar region and the upper tibia of the knee, respectively, thereby firmly supporting the knee against anterior tibial displacements. The specific mounting configuration of the V-shaped strap 52 and its specific elastic properties result in a support force whose direction does not change, and whose magnitude either stays the same or increases slightly as the knee is bent. Additionally, the combination of the support given to the knee as a whole by the condyle supporting portion 16, the sidebars 5, 6, and the upper and lower support assemblies 9, 11 of the orthosis, protect the leg from varus, valgus, and rotary instabilities, as well as hyper-extension. Additionally, the foam neoprene lining 19 of the pad assembly 19, in combination with the foam neoprene straps 24, 44 and stocking 18 of the wearer help to prevent the orthosis from slipping out of position on the wearer's leg during vigorous physical activity.

Figures 3, 4:
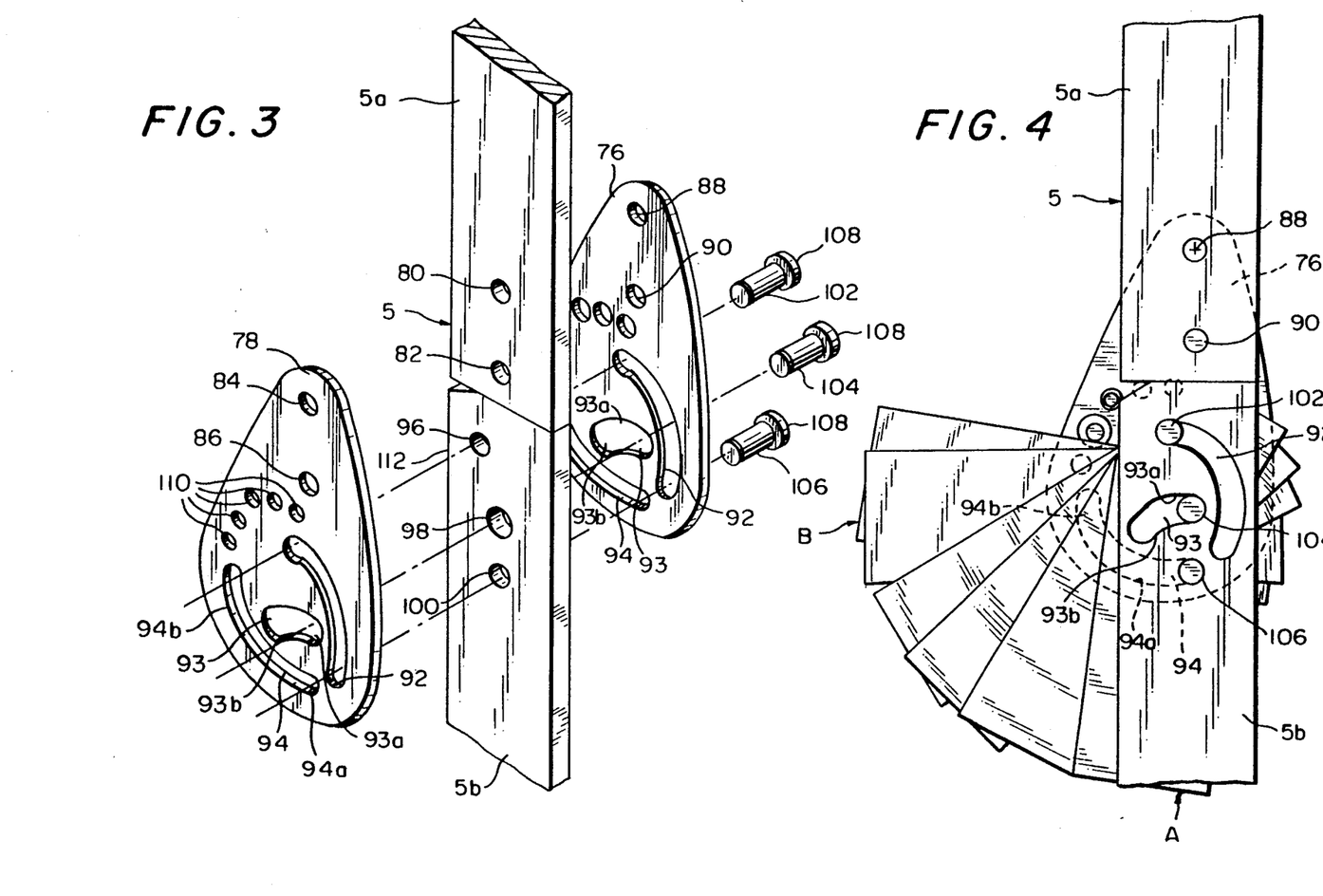
FIG. 3 is an exploded perspective view of the inventive hinge.
FIG. 4 is a view of the inventive hinge, with one of the plates removed, showing the angular movement of the hinge.

FIG. 3 shows the hinge 7 as consisting of first and second plates 76, 78 which have, for example, the upper and lower portions 5a, 5b of the sidebar 5 disposed therebetween. The upper portion 5a has a pair of holes 80, 82 which correspond to holes 84 and 86, respectively, in plate 78, and holes 88, 90, respectively, in plate 76. Pins (not shown) or other conventional connecting devices pass through the corresponding holes 88, 80, 84, and 90, 82, 86, thereby fixing upper portion 5a between plates 76, 78.

Cam slots 92, 93 and 94 are disposed in plate 78 while corresponding cam slots 92, 93 and 94 are disposed in plate 76. Moreover, the lower portion 5b of sidebar 5 has three holes 96, 98 and 100 which are aligned with the cam slots 92, 93 and 94, respectively. When the cam slots and holes in the lower portion 5b are thus aligned, cam-follower pins 102, 104 and 106 are received in the aligned cam slots and lower portion holes (92, 96), (93, 98), and (94, 100), respectively. The cam-follower pins 102, 104 and 106 are shown as hollow tubular rivets which have a threaded portion (not shown) therein which is designed to receive a screw (not shown). The cam-follower pins 102, 104, 106 each have a mushroomed end 108 such that when the cam-follower pins pass through their respective cam slots and sidebar holes, and a screw is subsequently screwed into the threaded portion from the end opposite the mushroom end, the cam plates 76, 78 are thereby aligned, and the lower portion 5b is free to rotate and move posteriorly with respect to the upper portion 5a as the cam-follower pins 102, 104, 106 move within their corresponding slots.

While the cam-follower pins have been shown as hollow tubular rivets, other similar fastening devices could be used. These fastening devices only need to be of a configuration such that when connected, they are free to slide within the cam slots. Moreover, the positioning of the plates 76, 78 and the depicted cam slots 92, 93, 94 are important in that they provide increased strength to the hinge, eliminate unwanted hinge movement, allow for proper alignment of the cam-follower pins and ensure the smooth movement of the cam-follower pins in the cam-slots in order to prevent binding of the hinge.

The movement of the lower portion 5b relative to the upper portion 5a is dictated by the shapes of the cam slots. As shown in FIGS. 3 and 4, cam slots 92 are long longitudinally oriented arcuate slots which are in the shape of a circular segment. Cam slots 93 are arcuate slots having a first segment 93a which extends substantially transversely to the longitudinal direction of the sidebar 5, and a second segment 93b which extends at an oblique angle from the first segment 93a. Cam slot 94 is an arcuate slot which has a first segment 94a which extends substantially transversely to the longitudinal direction of the sidebar 5, and a second segment 94b which is close to the shape of a circular segment.

The flexion movement of the lower portion 5b relative to the upper portion 5a is reflected in FIG. 4. That is, the fully extended position is reflected by the arrow A while the maximum flexion position is denoted by the arrow B. Intermediate degrees of flexion movement are also shown. Typically, the full range of flexion of the human knee (as indicated between positions A and B) is approximately 120°.

Figure 5:
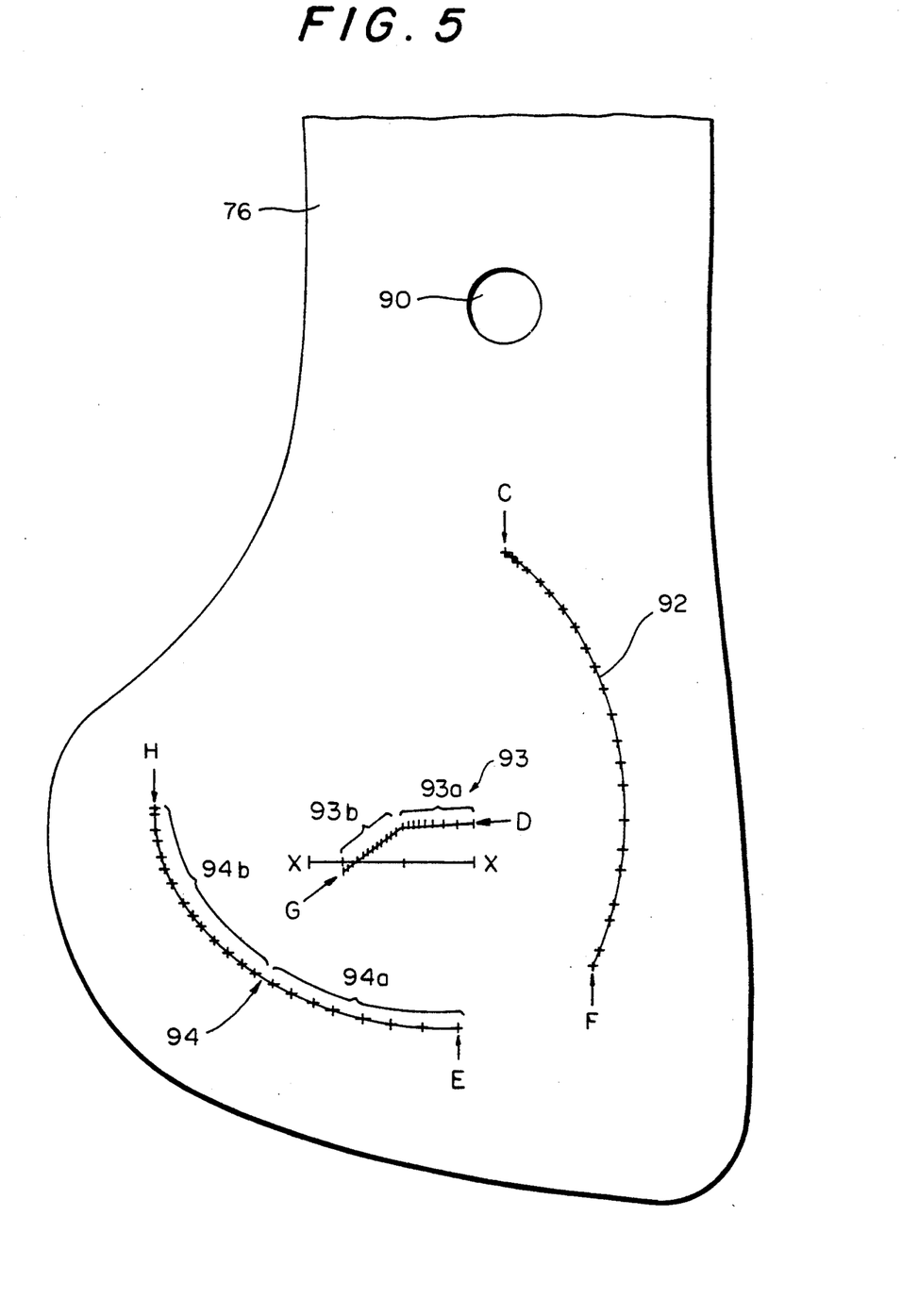
FIG. 5 is an enlarged view of a portion of a plate schematically showing the movement of the cam-follower pins during the flexion movement of the hinge.

FIG. 5 shows, in more detail, the actual positioning of each of the cam follower pins 102, 104, 106 as the lower portion 5b moves through the full range of flexion between points A and B. When the lower portion 5a is in the fully extended position A, the cam-follower pins 102, 104 and 106 are in the positions indicated by the arrows C, D and E, respectively, which corresponds to the position of arrow A in FIG. 4. However, as the lower portion 5b moves through the flexion range of motion, the cam-follower pins 102, 104 and 106 move from their starting positions toward finishing positions indicated by arrows F, G, H, respectively, which corresponds to the position indicated by arrow B of FIG. 4. The hash marks shown along the arcuate slots 92, 93 and 94 are illustrative of the relative positions of the cam-follower pins 102, 104, 106 at respective points during the flexion movement of the lower portion 5b from point A to point B. FIG. 5 clearly shows that as cam-follower pins 104, 106 move, respectively, within their substantially transverse segments 93a and 94a, they are changing their position at a much faster rate than the change of position of cam-follower pin 102 within cam slot 92. The relative movement of the cam-follower pins 102, 104, 106 during this period, directly translates into a rapid posterior movement of the lower portion 5b, relative to upper portion 5a. That is, horizontal line X—X has been drawn to show the horizontal posterior movement of cam-follower pin 104 as it moves within cam-slot 93. Accordingly, as cam-follower pin 104 moves through its first segment 93a, cam-follower pin 104 (and therefore lower portion 5b) moves posteriorly approximately 6 mm relative to upper portion 5a. Moreover, this 6 mm movement corresponds approximately to the first 40° of flexion as measured during the rotation from point A toward point B in FIG. 4.

However, when cam follower pin 104 begins to enter the second segment 93b, cam-follower pin 106 enters the second segment 94b such that the relative movement of cam-follower pins 104 and 106, within their respective cam slots, is much less than the movement of cam-follower pin 102 within cam slot 92.

Thus, because of the obtuse angle of second segment 93b, as cam-follower pin 104 moves within second segment 93b, the cam-follower pin 104 and the lower portion 5b only move posteriorly approximately an additional 4 mm, (after lower portion 5b has rotated the initial 40°), during the remaining 80° of flexion movement to point B. Therefore, since the position of cam-follower pin 104 is constantly changing throughout the full range of flexion movement, the axis of rotation of the lower portion 5b is constantly changing. Moreover, throughout the entire flexion movement, the lower portion 5b is constantly sliding in a posterior direction relative to the upper portion 5a.

The above movement of the inventive device thus more accurately mimics the natural movement of the human knee joint thereby providing for a better mechanical joint. In addition, the recited relationship of the posterior movement of the lower portion 5b, as related to the degree of flexion movement, is determined based on the approximate average movement of the medial side of the knee and the lateral side of the knee at any particular degree of flexion.

Another feature which can be incorporated in the invention concerns a means for limiting the extent of angular movement of the lower portion 5b relative to the upper portion 5a. This means for limiting the angular movement at lower portion 5b is reflected in FIG. 3, and consists of a series of flexion/extension holes 110 which are disposed in the plates 76, 78.

The flexion/extension holes 110 can be any suitable number, each of the holes being positioned to limit the angular movement of the lower portion 5b relative to the upper portion 5a in either the flexion or extension direction to a specified degree. Once the holes are in place, a respective limiting angle is chosen depending on the limiting motion desired, and a pin (not shown) or similar device, is inserted through the corresponding flexion/extension holes 110 in the plates 76 78. Thus, as lower portion 5b rotates, a lower surface 112 of lower portion 5b will make contact with the pin, preventing further angular movement of lower portion 5b.

While several embodiments of the invention have been described, it will be understood that further modifications are still capable, and this application is intended to cover any variations, use or adaptation of the invention and including such departures from the present disclosure as to come within the knowledge of customary practice in the art to which the invention pertains, and as may be applied to the essential features hereinbefore set forth and following within the scope of the invention and the limits of the appended claims.

What is claimed is:

1. A hinge for a brace having a sidebar with an upper portion and a lower portion, said hinge comprising:
   first and second plates, each of said first and second plates having a plurality of cam slots disposed therein and being connected to the upper and lower portions of the sidebar; and
   a plurality of cam pin followers each extending through said first and second plates and the lower portion of the sidebar such that said plurality of cam pin followers cooperate with said plurality of cam slots in said first and second plates to allow the lower portion of the sidebar to rotate through a predetermined angular range relative to the upper portion of the sidebar whereby an axis of rotation of the lower portion of the sidebar is constantly changing as the lower portion of the sidebar moves throughout said predetermined angular range;
   wherein a first cam slot of said plurality of cam slots in each of said first and second plates has a first segment which is substantially transverse relative to the longitudinal direction of the lower portion of the sidebar, and a second segment which is directed away from said first segment at an obtuse angle.

2. A hinge according to claim 1, wherein the lower portion of the sidebar has a plurality of holes disposed therein, each of said cam pin followers being disposed in a respective one of said plurality of holes and in a respective one of said plurality of cam slots in each of said first and second plates.

3. A hinge according to claim 2, wherein a second cam slot of said plurality of cam slots in each of said first and second plates has a first section which is substantially transverse to the longitudinal direction of the lower portion of the sidebar, and a second section which is arcuately shaped.

4. A hinge for a brace having an upper portion and a lower portion, said hinge comprising:
   first and second plates, each of said first and second plates having a plurality of cam slots disposed therein and being connected to the upper and lower portions of the brace; and
   a plurality of cam pin followers each being connected to said first and second plates and the lower portion of the brace such that said plurality of cam pin followers cooperate with said plurality of cam slots in said first and second plates to allow the lower portion of the brace to rotate through a predetermined angular range relative to the upper portion of the brace whereby an axis of rotation of the lower portion of the brace is constantly changing as the lower portion of the brace is constantly changing as the lower portion of the brace moves throughout said predetermined angular range;
   wherein a first cam slot of said plurality of cam slots in each of said first and second plates has a first segment which is substantially transverse relative to the longitudinal direction of the lower portion of the brace, and a second segment which is directed away from said first segment at an obtuse angle;
   wherein the lower portion of the brace has a plurality of holes disposed therein, each of said cam pin followers being disposed in a respective one of said plurality of holes and in a respective one of said plurality of cam slots in each of said first and second plates;
   wherein a second cam slot of said plurality of cam slots in each of said first and second plates has a first section which is substantially transverse to the longitudinal direction of the lower portion of the brace, and a second section which is arcuately shaped;
   wherein a third cam slot of said plurality of cam slots in each of said first and second plates is arcuately shaped.

5. A hinge according to claim 4 wherein said first cam slots are disposed between said second and third cam slots.

6. A hinge according to claim 5, wherein said plurality of cam pin followers include first, second and third cam pin followers which are disposed, respectively, in said first, second and third cam slots of each of said first and second plates.

7. A hinge according to claim 6, wherein when said first cam pin follower moves the entire length of said first segment of said first cam slot, the lower portion of the brace moves posteriorly a first distance of approximately 6 mm with respect to the upper portion of the brace.

8. A hinge according to claim 7, wherein when said first cam pin follower moves the entire length of said second segment of said first cam slot, the lower portion of the brace moves posteriorly a second distance of approximately 4 mm with respect to the upper portion of the brace.

9. A hinge according to claim 8, wherein the movement of the lower portion of the brace said first and second distances corresponds to a rotation of the lower portion of the brace approximately 40° and 120°, respectively, relative to the upper portion of the brace.

10. A hinge for a brace having a sidebar with an upper portion and a lower portion, said hinge comprising:
    first and second plates, each of said first and second plates having a plurality of cam slots disposed therein and being connected to the upper and lower portions of the sidebar; and a plurality of cam pin followers each extending through said first and second plates and the lower portion of the sidebar such that said plurality of cam pin followers cooperate with said plurality of cam slots in said first and second plates, thereby permitting the lower portion of the sidebar to rotate through a predetermined angular range relative to the upper portion of the sidebar such that during an initial angle of rotation the lower portion of the sidebar moves substantially horizontally to the posterior a first distance relative to the upper portion of the sidebar, and during a rotation of the lower portion of the sidebar beyond said initial angle of rotation and up to the end of said predetermined angular range, the lower portion of the sidebar moves substantially horizontally to the posterior a second distance relative to the upper portion of the sidebar;

wherein a first cam slot of said plurality of cam slots in each of said first and second plates has a first segment which is substantially transverse relative to the longitudinal direction of the lower portion of the sidebar, and a second segment which is directed away from said first segment at an obtuse angle.

11. A hinge according to claim 10, wherein the lower portion of the sidebar has a plurality of holes disposed therein, each of said cam pin followers being disposed in a respective one of said plurality of holes and in a respective one of said plurality of cam slots in each of said first and second plates.

12. A hinge according to claim 11, wherein said first distance is approximately 6 mm and said second distance is approximately 4 mm.

13. A hinge according to claim 12, wherein said initial angle of rotation is approximately 40° and said predetermined angular range is approximately 0° to 120°.

14. A hinge according to claim 13, wherein a second cam slot of said plurality of cam lots in each of said first and second plates has a first section which is substantially transverse to the longitudinal direction of the lower portion of the brace and a second section which is arcuately shaped.

15. A hinge for a brace having an upper portion and a lower portion, said hinge comprising:

first and second plates, each of said first and second plates having a plurality of cam slots disposed therein and being connected to the upper and lower portions of the brace; and a plurality of cam pin followers each being connected to said first and second plates and the lower portion of the brace such that said plurality of cam pin followers cooperate with said plurality of cam slots in said first and second plates, thereby permitting the lower portion of the brace to rotate through a predetermined angular range relative to the upper portion of the brace such that during an initial angle of rotation the lower portion of the brace moves posteriorly a first distance relative to the upper portion of the brace, and during a rotation of the lower portion of the brace beyond said initial angle of rotation and up to the end of said predetermined angular range, the lower portion of the brace moves posteriorly a second distance relative to the upper portion of the brace;

wherein a first cam slot of said plurality of cam slots in each of said first and second plates has a first segment which is substantially transverse relative to the longitudinal direction of the lower portion of the brace, and a second segment which is directed away from said first segment at an obtuse angle;

wherein the lower portion of the brace has a plurality of holes disposed therein, each of said cam pin followers being disposed in a respective one of said plurality of holes and in a respective one of said plurality of cam slots in each of said first and second plates;

wherein said first distance is approximately 6 mm and said second distance is approximately 4 mm;

wherein said initial angle of rotation is approximately 40° and said predetermined angular range is approximately 0° to 120°;

wherein a second cam slot of said plurality of cam slots in each of said first and second plates has a first section which is substantially transverse to the longitudinal direction of the lower portion of the brace and a second section which is arcuately shaped;

wherein a third cam slot of said plurality of cam slots in each of said first and second plates is arcuately shaped.

16. A hinge according to claim 15, wherein said first cam slots are disposed between said second and third cam slots.

17. A hinge according to claim 16, wherein said plurality of cam pin followers includes first, second and third cam pin followers which are disposed, respectively, in said first, second and third cam slots of each of said first and second plates.

18. A hinge according to claim 17, wherein when said first cam pin follower moves the entire length of said first segment of said first cam slot, the lower portion of the brace moves posteriorly said first distance, said first distance being approximately 6 mm; and wherein when said first cam pin follower moves the entire length of said second segment of said first cam slot, the lower portion of the brace moves posteriorly said second distance, said second distance being approximately 4 mm.

19. A hinge for a brace having an upper portion and a lower portion, said hinge comprising:

first and second plates, each of said first and second plates having at least three cam slots disposed therein and being connected to the upper and lower portions of the brace; and three cam pin followers each being connected to said first and second plates and the lower portion of the brace such that each of the cam pin followers cooperate with a respective one of the three cam slots in each of said first and second plates to allow the lower portion of the brace to rotate through a predetermined angular range relative to the upper portion of the brace whereby an axis of rotation of the lower portion of the brace is constantly changing as the lower portion of the brace moves throughout said predetermined angular range;

wherein a first cam slot of said three cam slots in each of said first and second plates has a first segment which is substantially transverse relative to the longitudinal direction of the lower portion of the brace, and a second segment which is directed away from said first segment at an obtuse angle.

* * * * *